United States Patent
Epshtein et al.

(10) Patent No.: US 8,936,593 B2
(45) Date of Patent: *Jan. 20, 2015

(54) DEVICE, APPARATUS, AND METHOD OF ADIPOSE TISSUE TREATMENT

(71) Applicants: Haim Epshtein, Benyamina (IL); Boris Vaynberg, Zikron Yaakov (IL)

(72) Inventors: Haim Epshtein, Benyamina (IL); Boris Vaynberg, Zikron Yaakov (IL)

(73) Assignee: Syneron Medical Ltd., Yokneam Illit (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/041,185

(22) Filed: Sep. 30, 2013

(65) Prior Publication Data

US 2014/0031803 A1 Jan. 30, 2014

Related U.S. Application Data

(62) Division of application No. 12/357,564, filed on Jan. 22, 2009, now Pat. No. 8,771,263.

(60) Provisional application No. 61/023,194, filed on Jan. 24, 2008, provisional application No. 61/085,424, filed on Aug. 1, 2008.

(51) Int. Cl.
*A61B 18/20* (2006.01)
*A61B 18/24* (2006.01)
(Continued)

(52) U.S. Cl.
CPC ............... *A61B 18/201* (2013.01); *A61B 18/24* (2013.01); *A61B 2017/00141* (2013.01);
(Continued)

(58) Field of Classification Search
CPC .............................. A61B 18/20; A61B 18/203
USPC ..................................... 606/9, 15; 607/88–90
See application file for complete search history.

(56) References Cited

U.S. PATENT DOCUMENTS

| 2,183,726 A | 2/1939 | Sommer et al. |
| 2,231,095 A | 2/1941 | Sommer et al. |

(Continued)

FOREIGN PATENT DOCUMENTS

| CA | 2495005 A1 | 2/2004 |
| CN | 1078383 A | 11/1993 |

(Continued)

OTHER PUBLICATIONS

Acne Clearance, LHE Clinical Casebook, Radiancy: Lighting the Future of Skin Care, © 2002.

(Continued)

*Primary Examiner* — William Thomson
*Assistant Examiner* — Jeffrey Lipitz
(74) *Attorney, Agent, or Firm* — Smith Risley Tempel Santos LLC; Gregory Scott Smith

(57) ABSTRACT

An improved procedure for performing liposuction is obtained by utilizing a needle that includes a laser source conductor with one end of the needle being configured for insertion into a target adipose skin volume and the other end being coupled to a laser source. The needle may include one or more channels for extracting the treated adipose area. A vacuum source can be used in the extraction of the treated adipose. Further, the first end of the needle may include a cap or end-piece that reduces the build up of carbon deposits. A temperature sensor may be used as input to adjust the laser power and prevent over exposure.

14 Claims, 5 Drawing Sheets

(51) Int. Cl.
  *A61B 17/00* (2006.01)
  *A61B 18/00* (2006.01)
  *A61M 1/00* (2006.01)

(52) U.S. Cl.
  CPC ............... *A61B 2017/00154* (2013.01); *A61B 2018/00464* (2013.01); *A61B 2018/2065* (2013.01); *A61M 1/008* (2013.01); *A61M 2202/08* (2013.01)
  USPC ............... 606/15; 606/9; 606/12; 606/13

(56) References Cited

U.S. PATENT DOCUMENTS

| | | |
|---|---|---|
| 2,824,308 A | 2/1958 | Duncan |
| 2,888,927 A | 6/1959 | Fozard |
| 3,088,205 A | 5/1963 | Ellis |
| D196,532 S | 10/1963 | Facci |
| 4,174,713 A | 11/1979 | Mehl |
| 4,182,329 A | 1/1980 | Smit et al. |
| 4,185,632 A | 1/1980 | Shaw |
| 4,200,104 A | 4/1980 | Harris |
| 4,211,230 A | 7/1980 | Woltosz |
| 4,321,926 A | 3/1982 | Roge |
| D269,294 S | 6/1983 | Rakocy et al. |
| D271,015 S | 10/1983 | Geraets |
| D271,199 S | 11/1983 | Geraets |
| D274,462 S | 6/1984 | Rakocy et al. |
| 4,532,924 A | 8/1985 | Auth et al. |
| 4,550,728 A | 11/1985 | Runyon et al. |
| 4,553,936 A | 11/1985 | Wang |
| 4,566,454 A | 1/1986 | Mehl et al. |
| 4,753,958 A | 6/1988 | Weinstein et al. |
| 4,784,135 A | 11/1988 | Blum et al. |
| 4,844,063 A | 7/1989 | Clark |
| 4,867,682 A | 9/1989 | Hammesfahr et al. |
| 4,869,584 A | 9/1989 | Dion |
| 4,940,456 A | 7/1990 | Sibalis et al. |
| 4,979,180 A | 12/1990 | Muncheryan |
| 5,016,999 A | 5/1991 | Williams |
| 5,087,240 A | 2/1992 | Sibalis |
| 5,125,928 A | 6/1992 | Parins et al. |
| 5,158,537 A | 10/1992 | Haak et al. |
| 5,169,384 A | 12/1992 | Bosniak et al. |
| 5,250,023 A | 10/1993 | Lee et al. |
| 5,286,479 A | 2/1994 | Garlich et al. |
| 5,316,473 A | 5/1994 | Hare |
| 5,348,554 A | 9/1994 | Imran et al. |
| 5,383,874 A | 1/1995 | Jackson et al. |
| 5,402,697 A | 4/1995 | Brooks |
| 5,406,340 A | 4/1995 | Hoff |
| 5,418,130 A | 5/1995 | Platz et al. |
| 5,487,662 A | 1/1996 | Kipke et al. |
| 5,509,916 A | 4/1996 | Taylor |
| 5,520,684 A | 5/1996 | Imran |
| 5,521,392 A | 5/1996 | Kennedy et al. |
| 5,582,476 A | 12/1996 | Hansen |
| 5,611,793 A | 3/1997 | Wilson et al. |
| 5,642,997 A | 7/1997 | Gregg et al. |
| 5,658,148 A | 8/1997 | Neuberger et al. |
| 5,674,191 A | 10/1997 | Edwards et al. |
| 5,681,282 A | 10/1997 | Eggers et al. |
| 5,683,380 A | 11/1997 | Eckhouse et al. |
| 5,693,052 A | 12/1997 | Weaver |
| 5,698,866 A | 12/1997 | Doiron et al. |
| 5,704,935 A | 1/1998 | Pahl et al. |
| 5,707,403 A | 1/1998 | Grove et al. |
| 5,718,702 A | 2/1998 | Edwards |
| 5,722,411 A | 3/1998 | Suzuki et al. |
| 5,735,844 A | 4/1998 | Anderson et al. |
| 5,769,880 A | 6/1998 | Truckai et al. |
| 5,776,092 A | 7/1998 | Farin et al. |
| 5,814,008 A | 9/1998 | Chen et al. |
| 5,824,023 A | 10/1998 | Anderson |
| 5,846,252 A | 12/1998 | Mehl, Sr. |
| 5,868,744 A | 2/1999 | Willmen |
| 5,871,469 A | 2/1999 | Eggers et al. |
| 5,873,855 A | 2/1999 | Eggers et al. |
| 5,888,198 A | 3/1999 | Eggers et al. |
| 5,935,143 A | 8/1999 | Hood |
| 5,949,514 A | 9/1999 | Wargon |
| 5,954,710 A | 9/1999 | Paolini et al. |
| 5,961,482 A | 10/1999 | Chien et al. |
| 5,983,130 A | 11/1999 | Phipps et al. |
| 5,983,135 A | 11/1999 | Avrahami |
| 5,984,915 A | 11/1999 | Loeb et al. |
| 5,993,180 A | 11/1999 | Westerhof et al. |
| 6,024,733 A | 2/2000 | Eggers et al. |
| 6,030,384 A | 2/2000 | Nezhat |
| 6,042,959 A | 3/2000 | Debe et al. |
| 6,056,548 A | 5/2000 | Neuberger et al. |
| 6,063,108 A | 5/2000 | Salansky et al. |
| 6,066,134 A | 5/2000 | Eggers et al. |
| 6,078,830 A | 6/2000 | Levin et al. |
| 6,080,127 A | 6/2000 | Li et al. |
| 6,080,391 A | 6/2000 | Tsuchiya et al. |
| 6,081,934 A | 7/2000 | Stefanovsky et al. |
| 6,097,976 A | 8/2000 | Yang et al. |
| 6,107,326 A | 8/2000 | Jori |
| 6,132,701 A | 10/2000 | Perez et al. |
| 6,148,232 A | 11/2000 | Avrahami |
| 6,159,222 A | 12/2000 | Yiu |
| 6,173,202 B1 | 1/2001 | Eppstein |
| 6,187,001 B1 | 2/2001 | Azar et al. |
| 6,190,609 B1 | 2/2001 | Chapman et al. |
| 6,191,110 B1 | 2/2001 | Jaynes et al. |
| 6,208,881 B1 | 3/2001 | Champeau |
| 6,210,402 B1 | 4/2001 | Olsen et al. |
| 6,221,095 B1 | 4/2001 | Van Zuylen et al. |
| 6,231,571 B1 | 5/2001 | Ellman et al. |
| 6,231,593 B1 | 5/2001 | Meserol |
| 6,251,127 B1 | 6/2001 | Biel |
| 6,256,525 B1 | 7/2001 | Yang et al. |
| 6,258,319 B1 | 7/2001 | Hearst et al. |
| 6,273,884 B1 | 8/2001 | Altshuler et al. |
| 6,275,728 B1 | 8/2001 | Venkatraman |
| 6,277,116 B1 | 8/2001 | Utely et al. |
| 6,280,438 B1 | 8/2001 | Eckhouse et al. |
| 6,288,498 B1 | 9/2001 | Cheng |
| 6,302,874 B1 | 10/2001 | Zhang et al. |
| 6,308,413 B1 | 10/2001 | Westerhof et al. |
| 6,325,797 B1 | 12/2001 | Stewart et al. |
| 6,343,400 B1 | 2/2002 | Massholder et al. |
| 6,343,933 B1 | 2/2002 | Montgomery et al. |
| 6,374,653 B1 | 4/2002 | Gokcebay et al. |
| 6,400,976 B1 | 6/2002 | Champeau |
| 6,406,157 B1 | 6/2002 | Audet |
| 6,413,255 B1 | 7/2002 | Stern |
| 6,419,674 B1 | 7/2002 | Bowser et al. |
| 6,433,343 B1 | 8/2002 | Cimino et al. |
| 6,440,121 B1 | 8/2002 | Weber et al. |
| 6,461,354 B1 | 10/2002 | Olsen et al. |
| 6,461,567 B1 | 10/2002 | Hearst et al. |
| 6,462,070 B1 | 10/2002 | Hasan et al. |
| 6,471,716 B1 | 10/2002 | Pecukonis |
| 6,477,410 B1 | 11/2002 | Henley et al. |
| 6,482,201 B1 | 11/2002 | Olsen et al. |
| 6,482,204 B1 | 11/2002 | Lax et al. |
| 6,487,447 B1 | 11/2002 | Weimann et al. |
| 6,490,482 B2 | 12/2002 | Mori et al. |
| 6,493,940 B2 | 12/2002 | Westerhof et al. |
| 6,494,900 B1 | 12/2002 | Salansky et al. |
| 6,497,702 B1 | 12/2002 | Bernaz |
| 6,508,813 B1 | 1/2003 | Altshuler |
| 6,510,341 B1 | 1/2003 | Kuribayashi et al. |
| 6,511,475 B1 | 1/2003 | Altshuler et al. |
| 6,514,243 B1 | 2/2003 | Eckhouse et al. |
| 6,514,248 B1 | 2/2003 | Eggers et al. |
| 6,517,532 B1 | 2/2003 | Altshuler et al. |
| 6,533,775 B1 | 3/2003 | Rizoiu |
| 6,544,259 B1 | 4/2003 | Tsaliovich |
| 6,544,261 B2 | 4/2003 | Ellsberry et al. |
| 6,558,653 B2 | 5/2003 | Andersen et al. |
| 6,572,637 B1 | 6/2003 | Yamazaki et al. |
| 6,582,429 B2 | 6/2003 | Krishnan et al. |

(56) References Cited

U.S. PATENT DOCUMENTS

| | | |
|---|---|---|
| 6,594,905 B2 | 7/2003 | Furst et al. |
| 6,595,947 B1 | 7/2003 | Mikszta et al. |
| 6,595,990 B1 | 7/2003 | Weinstein et al. |
| 6,597,946 B2 | 7/2003 | Avrahami et al. |
| 6,602,245 B1 | 8/2003 | Thiberg |
| 6,611,706 B2 | 8/2003 | Avrahami et al. |
| 6,611,707 B1 | 8/2003 | Prausnitz et al. |
| 6,612,819 B1 | 9/2003 | Furst et al. |
| 6,615,079 B1 | 9/2003 | Avrahami |
| 6,618,620 B1 | 9/2003 | Freundlich et al. |
| 6,620,158 B2 | 9/2003 | Ronci |
| 6,623,454 B1 | 9/2003 | Eggers et al. |
| 6,629,974 B2 | 10/2003 | Penny et al. |
| 6,632,002 B1 | 10/2003 | Chubb et al. |
| 6,632,193 B1 | 10/2003 | Davison et al. |
| 6,632,220 B1 | 10/2003 | Eggers et al. |
| 6,637,877 B1 | 10/2003 | Hartley et al. |
| 6,659,106 B1 | 12/2003 | Hovda et al. |
| 6,663,620 B2 | 12/2003 | Altshuler et al. |
| 6,676,655 B2 | 1/2004 | McDaniel |
| 6,678,554 B1 | 1/2004 | Sun et al. |
| 6,702,808 B1 | 3/2004 | Kreindel |
| 6,708,060 B1 | 3/2004 | Avrahami et al. |
| 6,711,435 B2 | 3/2004 | Avrahami |
| 6,719,754 B2 | 4/2004 | Underwood et al. |
| 6,723,092 B2 | 4/2004 | Brown et al. |
| D490,156 S | 5/2004 | Fischer et al. |
| D490,526 S | 5/2004 | Jonsen |
| 6,740,079 B1 | 5/2004 | Eggers et al. |
| 6,743,211 B1 | 6/2004 | Prausnitz et al. |
| 6,758,845 B1 | 7/2004 | Weckwerth et al. |
| 6,761,729 B2 | 7/2004 | Babaev |
| 6,767,341 B2 | 7/2004 | Cho |
| 6,770,069 B1 | 8/2004 | Hobart et al. |
| 6,773,431 B2 | 8/2004 | Eggers et al. |
| 6,780,838 B2 | 8/2004 | Lipton et al. |
| RE38,643 E | 11/2004 | Sugaya et al. |
| 6,887,260 B1 | 5/2005 | McDaniel |
| 6,905,496 B1 | 6/2005 | Ellman et al. |
| 6,974,450 B2 | 12/2005 | Weber et al. |
| 7,006,874 B2 | 2/2006 | Knowlton et al. |
| 7,022,121 B2 | 4/2006 | Stern et al. |
| 7,077,840 B2 | 7/2006 | Altshuler et al. |
| 7,115,123 B2 | 10/2006 | Knowlton et al. |
| 7,118,563 B2 | 10/2006 | Weckwerth et al. |
| 7,141,049 B2 | 11/2006 | Stern et al. |
| 7,153,298 B1 | 12/2006 | Cohen |
| 7,234,239 B2 | 6/2007 | Saito et al. |
| 7,238,183 B2 | 7/2007 | Kreindel |
| 7,251,531 B2 | 7/2007 | Mosher et al. |
| 7,275,819 B2 | 10/2007 | Bleau |
| 7,278,993 B2 | 10/2007 | Kelly et al. |
| 7,435,247 B2 | 10/2008 | Woloszko et al. |
| 7,494,488 B2 | 2/2009 | Weber |
| 7,517,344 B2 | 4/2009 | Van Hal et al. |
| 7,643,874 B2 | 1/2010 | Nitzan et al. |
| 7,713,266 B2 | 5/2010 | Elkins et al. |
| 7,771,419 B2 | 8/2010 | Carmel et al. |
| 7,824,394 B2 | 11/2010 | Manstein |
| 7,935,107 B2 | 5/2011 | Altshuler et al. |
| 8,021,360 B2 | 9/2011 | Dunning et al. |
| 8,034,052 B2 | 10/2011 | Podhajsky |
| 8,109,927 B2 | 2/2012 | Kelly et al. |
| 8,128,622 B2 | 3/2012 | Podhajsky et al. |
| 8,133,191 B2 | 3/2012 | Rosenberg et al. |
| 8,133,216 B2 | 3/2012 | Knopp et al. |
| 8,157,807 B2 | 4/2012 | Ferren et al. |
| 8,202,268 B1 | 6/2012 | Wells et al. |
| 8,206,381 B2 | 6/2012 | Lischinsky et al. |
| 8,235,989 B2 | 8/2012 | Palanker et al. |
| 8,273,037 B2 | 9/2012 | Kreindel et al. |
| 8,292,882 B2 | 10/2012 | Danek et al. |
| 8,506,564 B2 | 8/2013 | Long et al. |
| 2001/0007068 A1 | 7/2001 | Ota et al. |
| 2001/0014819 A1 | 8/2001 | Ingle et al. |
| 2002/0010414 A1 | 1/2002 | Coston et al. |
| 2002/0035363 A1 | 3/2002 | Edwards et al. |
| 2002/0058936 A1 | 5/2002 | Avrahami et al. |
| 2002/0082543 A1 | 6/2002 | Park et al. |
| 2002/0104543 A1 | 8/2002 | Hollander et al. |
| 2002/0120256 A1 | 8/2002 | Furuno et al. |
| 2002/0120260 A1 | 8/2002 | Morris et al. |
| 2002/0120261 A1 | 8/2002 | Morris et al. |
| 2002/0128641 A1 | 9/2002 | Underwood et al. |
| 2002/0128648 A1 | 9/2002 | Weber et al. |
| 2002/0161324 A1 | 10/2002 | Henley et al. |
| 2002/0173780 A1 | 11/2002 | Altshuler et al. |
| 2002/0183245 A1 | 12/2002 | Hasan et al. |
| 2002/0190337 A1 | 12/2002 | House et al. |
| 2002/0193729 A1 | 12/2002 | Cormier et al. |
| 2002/0198575 A1 | 12/2002 | Sullivan |
| 2003/0004499 A1 | 1/2003 | McDaniel |
| 2003/0018255 A1 | 1/2003 | Martin et al. |
| 2003/0032950 A1 | 2/2003 | Altshuler et al. |
| 2003/0055413 A1 | 3/2003 | Altshuler et al. |
| 2003/0055414 A1 | 3/2003 | Altshuler et al. |
| 2003/0109871 A1 | 6/2003 | Johnson et al. |
| 2003/0185255 A1 | 10/2003 | Ye et al. |
| 2003/0195494 A1 | 10/2003 | Altshuler et al. |
| 2003/0199863 A1 | 10/2003 | Swanson et al. |
| 2003/0199946 A1 | 10/2003 | Gutwein |
| 2004/0010250 A1 | 1/2004 | Manna et al. |
| 2004/0010298 A1 | 1/2004 | Altshuler et al. |
| 2004/0015161 A1 | 1/2004 | Lovewell |
| 2004/0015162 A1 | 1/2004 | McGaffigan |
| 2004/0064167 A1 | 4/2004 | Berry et al. |
| 2004/0133251 A1 | 7/2004 | Altshuler et al. |
| 2004/0138603 A1 | 7/2004 | Cleary et al. |
| 2004/0143308 A1 | 7/2004 | Lundahl |
| 2004/0167501 A1 | 8/2004 | Island et al. |
| 2004/0181216 A1 | 9/2004 | Kelly et al. |
| 2004/0193234 A1 | 9/2004 | Butler |
| 2004/0210214 A1 | 10/2004 | Knowlton |
| 2004/0236320 A1 | 11/2004 | Protsenko et al. |
| 2004/0260210 A1 | 12/2004 | Ella et al. |
| 2004/0267252 A1 | 12/2004 | Washington et al. |
| 2005/0015042 A1 | 1/2005 | Sun et al. |
| 2005/0033286 A1 | 2/2005 | Eggers et al. |
| 2005/0043653 A1 | 2/2005 | Trimmer et al. |
| 2005/0049543 A1 | 3/2005 | Anderson et al. |
| 2005/0085804 A1 | 4/2005 | McGaffigan |
| 2005/0096646 A1 | 5/2005 | Wellman et al. |
| 2005/0137654 A1 | 6/2005 | Hoenig et al. |
| 2005/0137655 A1 | 6/2005 | MacFarland et al. |
| 2005/0147137 A1 | 7/2005 | Slatkine |
| 2005/0149012 A1 | 7/2005 | Penny et al. |
| 2005/0177139 A1 | 8/2005 | Yamazaki et al. |
| 2005/0288680 A1 | 12/2005 | Ingle et al. |
| 2006/0036300 A1 | 2/2006 | Kreindel |
| 2006/0058712 A1 | 3/2006 | Altshuler et al. |
| 2006/0130675 A1 | 6/2006 | Crawford |
| 2006/0200213 A1 | 9/2006 | McDaniel |
| 2006/0224148 A1* | 10/2006 | Cho et al. .................. 606/15 |
| 2006/0231568 A1 | 10/2006 | Lynn et al. |
| 2006/0247741 A1 | 11/2006 | Hsu et al. |
| 2006/0253112 A1 | 11/2006 | Suarez et al. |
| 2006/0271028 A1 | 11/2006 | Altshuler et al. |
| 2007/0009542 A1 | 1/2007 | Levin et al. |
| 2007/0016117 A1 | 1/2007 | Sliwa et al. |
| 2007/0038206 A1 | 2/2007 | Altshuler et al. |
| 2007/0093798 A1 | 4/2007 | Debenedictis et al. |
| 2007/0106349 A1 | 5/2007 | Karni et al. |
| 2007/0129711 A1 | 6/2007 | Altshuler et al. |
| 2007/0142881 A1* | 6/2007 | Hennings .................. 607/89 |
| 2007/0191821 A1 | 8/2007 | Boxer Wachler |
| 2007/0191827 A1 | 8/2007 | Lischinsky et al. |
| 2007/0197895 A1 | 8/2007 | Nycz et al. |
| 2007/0198004 A1 | 8/2007 | Altshuler et al. |
| 2007/0213696 A1 | 9/2007 | Altshuler et al. |
| 2007/0239142 A1 | 10/2007 | Altshuler et al. |
| 2007/0239143 A1 | 10/2007 | Altshuler et al. |
| 2007/0239152 A1 | 10/2007 | Trezon |
| 2007/0264626 A1* | 11/2007 | DeBenedictis et al. ........ 435/4 |
| 2007/0271714 A1 | 11/2007 | Adam et al. |

(56) References Cited

U.S. PATENT DOCUMENTS

| | | | |
|---|---|---|---|
| 2007/0293849 A1* | 12/2007 | Hennings et al. ............ | 606/9 |
| 2008/0004678 A1 | 1/2008 | Kreindel | |
| 2008/0123238 A1 | 5/2008 | Campos et al. | |
| 2008/0139974 A1 | 6/2008 | Da Silva | |
| 2008/0183167 A1 | 7/2008 | Britva et al. | |
| 2008/0188846 A1 | 8/2008 | Palanker et al. | |
| 2008/0200910 A1 | 8/2008 | Burger et al. | |
| 2008/0214986 A1 | 9/2008 | Ivorra et al. | |
| 2008/0214988 A1 | 9/2008 | Altshuler et al. | |
| 2008/0215124 A1 | 9/2008 | Wagenaar et al. | |
| 2008/0221504 A1 | 9/2008 | Aghion | |
| 2008/0274166 A1 | 11/2008 | Sacks et al. | |
| 2008/0294153 A1 | 11/2008 | Allshuler et al. | |
| 2008/0306476 A1 | 12/2008 | Hennings et al. | |
| 2009/0036953 A1 | 2/2009 | Gustavsson | |
| 2009/0043293 A1 | 2/2009 | Pankratov et al. | |
| 2009/0105706 A1 | 4/2009 | Livneh | |
| 2009/0112205 A1 | 4/2009 | McGill et al. | |
| 2009/0171341 A1 | 7/2009 | Pope et al. | |
| 2009/0182315 A1* | 7/2009 | Zigan et al. ............ | 606/15 |
| 2009/0192503 A1 | 7/2009 | Epshtein et al. | |
| 2009/0222023 A1 | 9/2009 | Boone et al. | |
| 2009/0234341 A1 | 9/2009 | Roth | |
| 2009/0234342 A1 | 9/2009 | Ely et al. | |
| 2009/0299361 A1 | 12/2009 | Flyash et al. | |
| 2010/0010480 A1 | 1/2010 | Mehta et al. | |
| 2010/0145321 A1 | 6/2010 | Altshuler et al. | |
| 2010/0185193 A1 | 7/2010 | Kreindel | |
| 2010/0198134 A1 | 8/2010 | Eckhouse | |
| 2010/0211055 A1 | 8/2010 | Eckhouse et al. | |
| 2010/0249772 A1 | 9/2010 | Mehta et al. | |
| 2011/0015549 A1 | 1/2011 | Eckhouse et al. | |
| 2011/0160712 A1* | 6/2011 | Tankovich et al. ............ | 606/9 |
| 2011/0166559 A1 | 7/2011 | Eckhouse et al. | |
| 2011/0196363 A1 | 8/2011 | Kreindel | |
| 2012/0016354 A9 | 1/2012 | Epshtein et al. | |
| 2012/0022435 A1 | 1/2012 | Ignon et al. | |
| 2012/0022504 A1 | 1/2012 | Epshtein et al. | |
| 2012/0022512 A1 | 1/2012 | Vaynberg | |
| 2012/0022518 A1 | 1/2012 | Levinson | |
| 2012/0123397 A1 | 5/2012 | Epshtein et al. | |
| 2012/0143178 A9 | 6/2012 | Mehta | |
| 2012/0197242 A1 | 8/2012 | Rosenberg | |
| 2012/0290023 A1 | 11/2012 | Boyden et al. | |
| 2013/0144280 A1 | 6/2013 | Eckhouse et al. | |
| 2013/0289679 A1 | 10/2013 | Eckhouse et al. | |

FOREIGN PATENT DOCUMENTS

| | | |
|---|---|---|
| EP | 0743029 B1 | 7/2002 |
| EP | 0824025 B1 | 11/2002 |
| GB | 2125986 A | 8/1982 |
| GB | 2202442 A | 9/1988 |
| JP | 04299998 A2 | 10/1992 |
| JP | 06113920 A2 | 4/1994 |
| JP | 11132843 A2 | 12/1999 |
| JP | 2003034630 | 2/2003 |
| WO | WO-93/21992 A1 | 11/1993 |
| WO | WO-9909143 A1 | 2/1999 |
| WO | WO-02078644 A2 | 10/2002 |
| WO | WO-03039367 A1 | 5/2003 |
| WO | WO 2007137304 A2 | 11/2007 |

OTHER PUBLICATIONS

Acne Star web page, describing "How to use get rid of Acne Treatment", printed May 5, 2005.
Acne Star web page, describing Clinical Studies, "The Treatment of acne vulgaris with a novel device that uses Gallium—Nitride diode light", printed May 5, 2005.
Aesthetic Buyers Guide: The Leading Cosmetic Practice Resource, Jan./Feb. 2004, vol. 7, No. I.
Bollen, CM. et al., "Full- versus partial-mouth disinfection in the treatment of periodontal infections. A pilot study: long-term microbiological observations", J Clin Periodontol Oct. 1996;23(10):960-70 (Abstract).
Bollen, CM. et al., "The effect of a one-stage full-mouth disinfection on different intra-oral niches. Clinical and microbiological observations", J Clin Periodontol Jan. 1998;25(1):56-66 (Abstract).
Calderi-Iead, R. Glen, "The Photobiology of LED Phototherapy".
Charakida et al., "Phototherapy in the Treatment of Acne Vulgaris, What is the Role?", Am. J. Clin. Dermatol 2004: 5(4): 211-216.
Cohen LR., "What causes bad breath?", University of Toronto; webpage (printed before Nov. 2, 2004).
Coventry et al. (2000) "ABC of oral health: Periodontal disease" British Medical Journal, 321, 36-39.
De Soete, M. et al., "One-stage full-mouth disinfection. Long-term microbiological results analyzed by checker board DNA-DNA hybridization", J Periodontol Mar. 2001; 72(3):374-82 (Abstract).
Elman M. et al., "The effective treatment of acne vulgaris by a high-intensity, narrow bank 405-420 nm light source", Cosmetic & Laser Ther 2003; 5: 111-116.
Flow Control Network web page, "Mini Diaphragm Pumps for Precision Dispensing" by Ping Lin, printed Aug. 2, 2005.
Friedberg JS et al., "Antibody-Targeted Photolysis Bacteriocidal Effects of Sn (IV) Chlonn e6-Dextran-Monoclonal Antibody Conjugates", Annals New York Academy of Sciences 618:383-393, 1991.
Greenstein G., Full-mouth therapy versus individual quadrant root planning: a critical commentary, JPeriodontol Jul. 2002;73(7):797-812 (Abstract).
Hamblin, M. et al., "Rapid Control of Wound Infections by Targeted Photodynamic Therapy Monitored by In Vivo Bioluminescence Imagining", Photochemistry and Photobiology, 2002, 75(1); 51-57.
Komerik et al. (2003) "In vivo killing of *Porphyromonas gingivalis* by toluidine blue-mediated Photosensitization in an animal model" Antimicrobial Agents and Chemotherapy, 47(3), 932-940.
Krespi, et al. (2005) "Lethal photosensitization of oral pathogens via red-filtered halogen lamp" Oral Diseases, 11(S1), 92-95.
Malik, Z. et al., "New Trends in Photobiology (Invited Review) Bactericidal Effects of Photoactivated Porphyrins—An Alternative Approach to Antimicrobial Drugs", Journal of Photochemistry and Photobiology, B: Biology, 5_1_1990}_281-293.
Matevski D. et al., "Lethal photosensitization of periodontal pathogens by a red-filtered Xenon lamp in invitro", JPeriodont. Res. 2003. 38:428-435.
Matevski D. et al., "Sensitivity of *Porphyromonas gingivalis* to Light-Activated Toluidine Blue O", University of Toronto, Faculty of Dentistry; Slide presentation (presented before Nov. 15, 2002).
Meisel etal. (2005) "Photodynamic therapy for periodontal diseases: State of the are" J. Photochem. Photobiol., 79, 159-170.
Mongardini, C. et al., "One stage full- versus partial-mouth disinfection in the treatment of chronic adult or generalized early-onset periodontitis. I. Long-term clinical observations", J Periodontol Jun. 1999;70(6):632-45 1Abstrac!2._.
Morton C.A. et al., An open study to determine the efficacy of blue light in the treatment of mild to moderate ance: preliminary data (publication status unknown).
Nakano et al. (2002) "Correlation between oral malodor and periodontal bacteria" Microbes Infect., 4(6), 679-683.
Ondine Biopharma web page—printed Oct. 15, 2002.
Papageorgiou et al., "Phototherapy with blue (415 nm) and red (660 nm) light in the treatment of acne vulgaris", British Journal of Dermatology 2000: 142: 973-978.
Pharmaceutical description, Levulan® Kerastick *arninolevulinic acid I-IC!) for Topical Solution, 20'X.
Quirynen, M. et al. "Full- vs. partial-mouth disinfection in the treatment of periodontal infections: short-term clinical and microbiological observations", J Dent Res Aug. 1995;74(8):1459-67 (Abstract).
Quirynen, M. et al., "The effect of a 1-stage full-mouth disinfection on oral malodor and microbial colonization of the tongue in periodontitis. A pilot study", J Periodontol Mar. 1998;69(3):374-82 (Abstract).
Quirynen, M. et al., "The intra-oral translocation of periodontopathogens jeopardises the outcome of periodontal therapy", Journal of Clincial Periodontology, Jun. 2001, vol. 28, Issue 6, p. 499 (Abstract).

(56) References Cited

OTHER PUBLICATIONS

Quirynen, M. et al., "The role of chlorhexidine in the one-stage full-mouth disinfection treatment of patients with advanced adult periodontitis. Long-term clinical and microbiological observations", J Clin Periodontol 2000 A1!JL2~579-89 J__Abstrac__!).

Quirynen. M. et al., "One stage full- versus partial-mouth disinfection in the treatment of chronic adult or generalized early-onset periodontitis. II. Long-term impact on microbial load", J Periodontol Jun. 1999;70(6):645-56 J__Abstrac!2.__.

Sanz et al. (2001) "Fundamentals of breath malodour" Journal of Contemporary Dental Practice, 2(4), 1-13.

Sarkar et al. (1993) "Lethal photosensitization of bacteria in subgingival plaque from patients with chronic periodontitis"J. Periodont. Res , 28, 204-21 O.

Skin91 I .corn web page regarding Peter Thomas Roth Clinical Acne Medication, acne treatment-Benzoyl Peroxide 5% pbp5, printed Apr. 19, 2005.

Soukos et al. (1998) "Targeted antimicrobial photochemotherapy", Antimicrobial Agents and Chemotherapy 42 ( 10 ), 2595-2601.

Spire Awarded Contract for Ear Surgery Laser—Press Release Aug. 23, 2002.

Temperatures.corn web page, "Thermistor Temperature Sensors," printed Aug. 2, 200.

Vandekerckhove, BN. et al.. "Full- versus partial-mouth disinfection in the treatment of periodontal infections. Long-term clinical observations of a pilot study", J Periodontol Dec. 1996;67(12):1251-9 (Abstract).

Wainwright M., Photodynamic antimicrobial chemotherapy (PACT), Journal of Antimicrobial Chemotherapy (1998) 42, 13-28.

Wilson (2005) "Lethal photosensitisation of oral bacteria and its potential application in the photodynamic therapy of oral infection" Photochem. Photobiol. Sci., 3, 412-418.

Wilson et al. (1995) "Bacteria in supragingival plaque samples can be killed by low-power laser light in the presence of a photosensitizer" J. Appl. Bacteriol., 78, 569-574.

Wood, et al. (1999) "An in vitro study of the use of photodynamic therapy for the treatment of natural oral plaque biofilrms formed in vivo" J. Photochem. Photogiol. B: Biol., 50, 1-7.

www.lightbioscience.com web page, Gentle Waves Cosmcceuticals, printed Jul. 29, 200.

www.lightbioscience.com web page, Gentle Waves LED Photomodulation Fact Sheet, printed Jul. 29, 2005.

PCT/IL08/01612 International Search Report.
PCT/IL09/00695 International Search Report.
PCT/IL09/00817 International Search Report.
PCT/IL09/00856 International Search Report.
PCT/IL10/00222 International Search Report.
PCT/IL2010/001025 International Search Report.

* cited by examiner

VIEW I-I

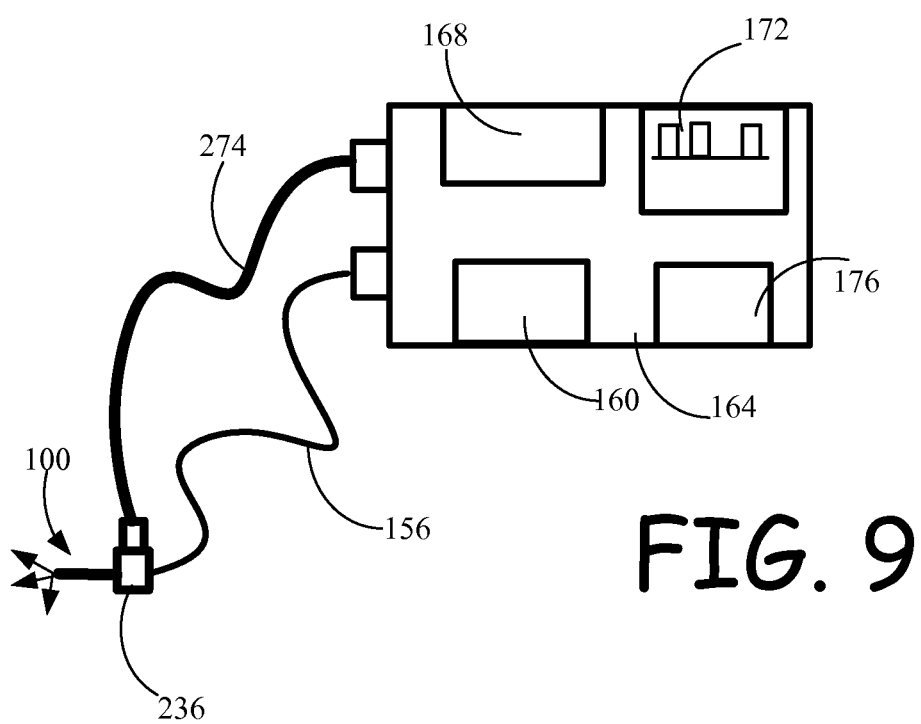

DEVICE, APPARATUS, AND METHOD OF ADIPOSE TISSUE TREATMENT

CROSS-REFERENCE TO RELATED APPLICATIONS

This application is a non-provisional application being filed under 37 CFR 1.53(b) and 35 USC 111 as a divisional of the presently pending U.S. patent application Ser. No. 12/357,564 filed on Jan. 22, 2009, which application claims priority to U.S. Provisional Application for Patents 61/023,194 filed on Jan. 24, 2008 and U.S. Provisional Application for Patents 61/085,424 filed on Aug. 1, 2008, all of which are hereby incorporated by reference.

BACKGROUND

The present device, apparatus, and method relate to the field of adipose tissue treatment and aesthetic body sculpturing.

Liposuction is a technique for removal of fat tissue from different sites in a particular human body. The process changes the external contours of the body and sometimes is described as body sculpturing. The fat is removed by a suction device via a cannula, or a small flexible tube inserted into a body cavity for draining off fluid or introducing medication, inserted into the appropriate site in the body. The process is painful and sometimes causes excessive bleeding.

Recently, liposuction procedures have been improved by the use of infrared laser radiation delivered through a fiber inserted into a cannula and introduced into the treated tissue site. Laser radiation liquefies the adipose tissue. The liquefied tissue is then removed by suction or may be left in the body, where it gradually dissipates. Laser assisted liposuction is considered to be a more advanced and minimally invasive procedure when compared to traditional liposuction techniques.

High temperature developed at the tip of the fiber causes frequent fiber tip carbonization, forcing the treatment provider to remove the fiber, clean the carbonized end or cleave the end and insert it back into the cannula for continued treatment. The cannula with the fiber also has to be removed for liquefied tissue suction performed through the same skin port. The fiber and the cannula have to be sterilized between the different processes and patients. Alternatively, a new sterile fiber and cannula would have to be used. All of the above restrictions have the effect of slowing down the process, increasing the treated subject discomfort and increasing the cost of the treatment.

Thus, there is a need in the art and the related industries for a suitable solution to these and other existing problems.

BRIEF SUMMARY

A variety of embodiments may be provided to achieve an improved technique to conduct liposuction of a target adipose tissue volume. For instance, one embodiment includes a needle with an inner core for conducting laser energy, with one end being configured for insertion into the target volume and the other end being coupleable to a laser source. The needle is inserted into the target volume of adipose tissue and at least one laser source connected to needle irradiates the target volume of the adipose tissue and melts the tissue. In some embodiments, two or more laser sources may be utilized with at least one laser source operating in a continuous operation mode and at least one laser source operating in a pulse operation mode. In such an embodiment, the laser operating in the continuous operation mode (CW) heats up the adipose tissue and the laser source operating in the pulse mode induces mechanical stress on the adipose tissue.

In some embodiments, a temperature probe may be utilized to monitor the temperature of the target volume of the adipose tissue and provide feedback to the laser source. Advantageously, this aspect results in allowing the at least one laser source to be adjusted avoid excessive damage to the target volume of adipose tissue.

These and other embodiments will be more fully appreciated by reviewing the detailed description and the related figures.

BRIEF DESCRIPTION OF THE SEVERAL VIEWS OF THE DRAWING

The disclosure is provided by way of non-limiting examples only, with reference to the accompanying drawings, wherein:

FIG. 9 is a schematic illustration of an additional exemplary embodiment of an apparatus for laser assisted liposuction employing the present needle.

DETAILED DESCRIPTION OF EMBODIMENTS OF THE INVENTION

Figure 1:
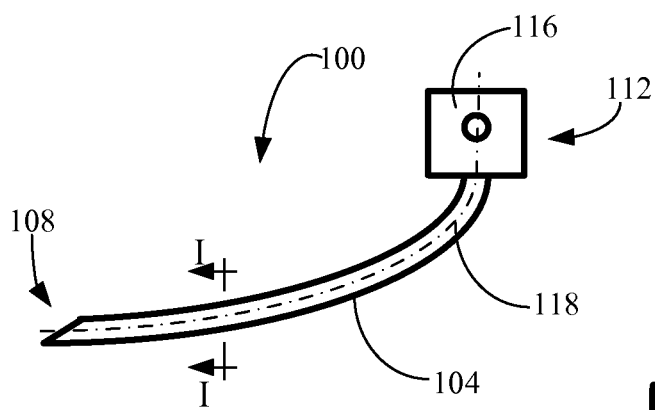
FIG. 1 is a schematic illustration of the first exemplary embodiment of a disposable laser radiation conveying needle.

The principles and execution of the device, apparatus, and method described herein may be understood with reference to the drawings, wherein like reference numerals denote like elements through the several views and the accompanying description of non-limiting, exemplary embodiments.

The term "needle," as used in the text of the present disclosure, means a flexible or rigid light guide configured to be inserted into the subject tissue to deliver laser radiation to a target volume of adipose tissue. In certain embodiments, the needle can be configured to withdraw liquid from the target volume in addition to the above stated uses.

The term adipose is known to those skilled in the art, and one non-limiting definition, provided for convenience only, includes fatty skin tissue, or skin tissue consisting of, resembling, or relating to fat. Adipose tissue is a type of connective tissue consisting of adipose cells, which are specialized to produce and store large fat globules. These globules are composed mainly of glycerol esters of oleic, palmitic, and stearic acids.

Reference is made to FIG. 1, which is a schematic illustration of the first exemplary embodiment of a disposable laser radiation conveying needle. Needle 100 is practically a needle shaped solid or hollow light conducting body 104 having a first end 108 and a second end 112 (In the context of the present disclosure "light" and "laser radiation" have the same meaning.). The first end 108 of needle 100 can be shaped for piercing and penetrating the skin of a subject (not shown) and the second end 112 of the needle 100, depending on the length of the needle 100, is adapted to connect directly to a source of laser radiation by means of fiber optics type connector 116 or with the help of an additional interim cable. The length of needle 100 may vary from a few millimeters to a few hundred millimeters and depends on the type of treatment required or being performed. The connection to the source of laser radiation may be performed by any type of fiber optics or similar type connectors. Line 118 designates the optical axis of needle 100.

Figure 2:
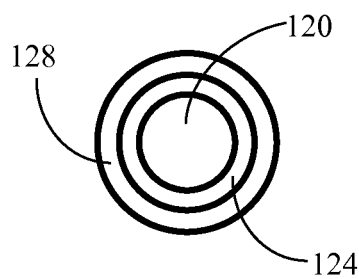
FIG. 2 is a schematic illustration of a cross section of the needle of FIG. 1.
Figure 3A:
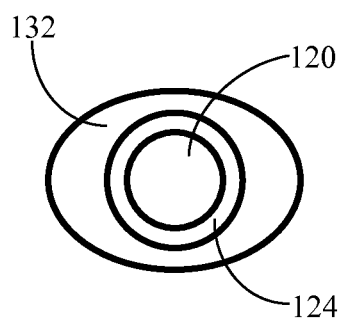
FIGS. 3A and 3B are schematic illustrations of additional exemplary needle cross sections.
Figure 3B:
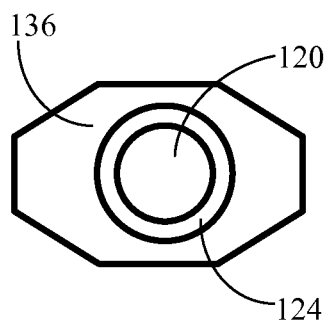

FIG. 2 is a cross section view of needle 100 taken at line I-I of FIG. 1, and is shown to have a round cross section. Needle 100 includes a solid light conducting core 120, a cladding 124 having a refractive index lower than core 120, and a protective jacket 128 that protects the sensitive fiber and provides the necessary stiffness to the needle 100. In some embodiments, as best shown in FIGS. 3B and 3C, a jacket 132 may have an elliptical shape (FIG. 3B) or the jacket 136 may have a polygonal (FIG. 3C) cross section. The diameter of core 120 can vary but operable embodiments may be 100 micron to 1500 micron, in some embodiments the diameter of cladding 124 may range from 200 micron to 2500 micron and the size of jacket 128, 132, and 136 may be 500 micron to 3000 micron or even more. Connection of needle body 104 to connector 116 may be performed by crimping, epoxy glue, or any other well known means that is established in the fiber optics industry.

First end 108 of needle 100 may be shaped for piercing the skin of a subject and may be terminated by a plane perpendicular to the optical axis 118 or oriented at an angle to the optical axis 118 of needle 100. Alternatively, end 108 may have a radius or an obtuse angle. In such case, a skin incision is made by any well known surgical means and the needle is introduced into the tissue through the skin incision. Other needle end 108 shapes that improve either skin penetration properties or laser power delivery quality are also possible and anticipated by various embodiments.

In an alternative embodiment, laser radiation emitted through the end of needle 100, assists needle 100 into the skin penetration process by providing a skin incision suitable for continuous or pulsed laser power. Such laser-performed incision may be advantageous in some aspects because it is accompanied by a simultaneous haemostatic effect, which coagulates the blood, reduces patient bleeding and shortens the recovery period.

Figure 4:
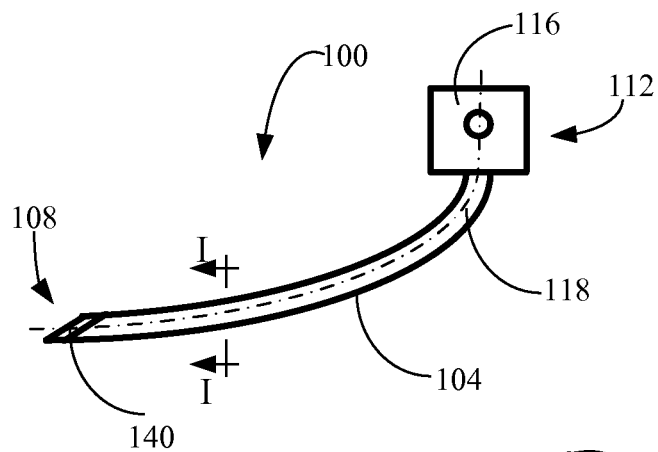
FIG. 4 is a schematic illustration of the second exemplary embodiment of a disposable laser radiation conveying needle with a carbonization resisting tip.

In a second exemplary embodiment of a disposable laser radiation conveying needle shown in FIG. 4, the first end 108 of needle 100 is terminated by a sapphire, YAG (Yttrium Aluminum Garnett), or diamond plate 140, or coating. During use, certain materials resulting from interaction of the tissue with high laser power, deposit on end 108 of needle 100. These carbonized deposits increase laser light absorption at the end 108 of needle 100 and this deposit should be periodically removed. Strong laser power absorption in carbonized deposit can increase local temperature at the end 108 resulting in needle damage. Sapphire, YAG, and diamond or other similar material are generally resistant to high temperature and their use as a termination of the first end 108 of needle 100 significantly improves needle life, and its carbonization resistance.

Figure 5:
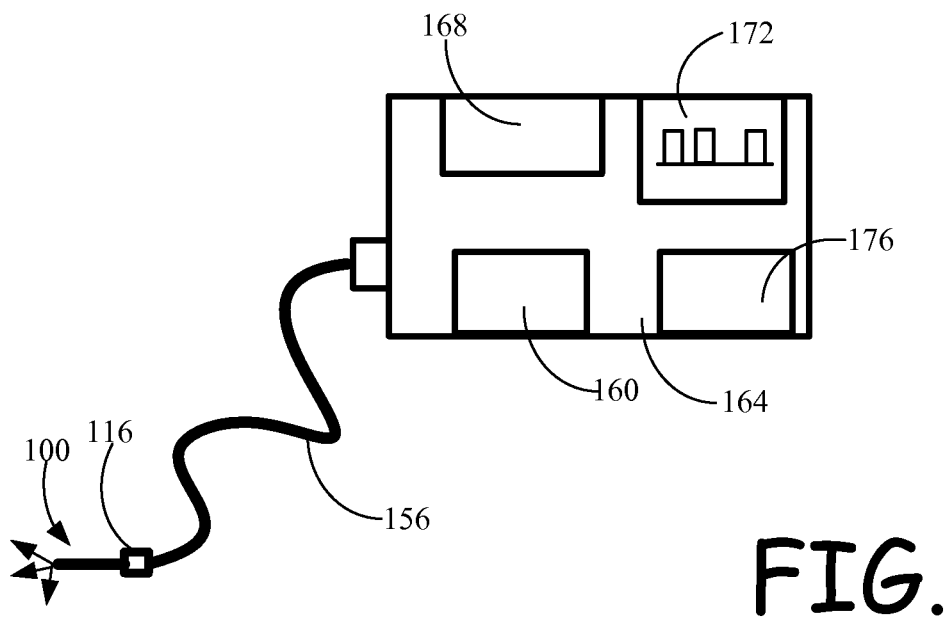
FIG. 5 is a schematic illustration of an exemplary embodiment of the apparatus for laser assisted liposuction employing the present needle.

FIG. 5 is a schematic illustration of an exemplary embodiment of an apparatus for laser assisted liposuction employing the illustrated embodiments, or other embodiments of the needle. Connector 116 connects needle 100 via an optical cable 156 to a source of laser radiation 160 configured to provide laser radiation emitted by one or more lasers incorporated in the source 160 to needle 100. Laser radiation source 160 may be packaged into a controller 164, or may be a stand alone unit. In some embodiments, needle 100 may be made long enough to connect directly to the source of laser radiation 160. In such cases, optical cable 156 may become redundant. Controller 164 may operate the source of laser radiation 160 in a pulse, continuous or other radiation mode.

Figure 6A:
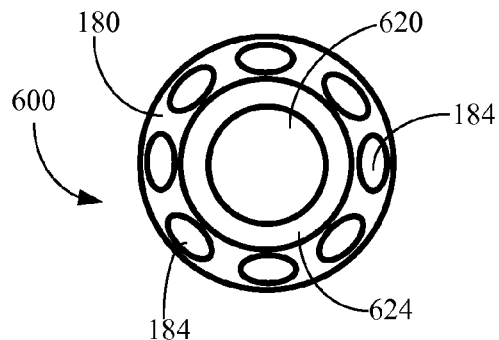
FIGS. 6A-6C are schematic illustrations of the third exemplary embodiment of a disposable laser radiation conveying needle with liquefied fat removal channels.
Figure 6B:
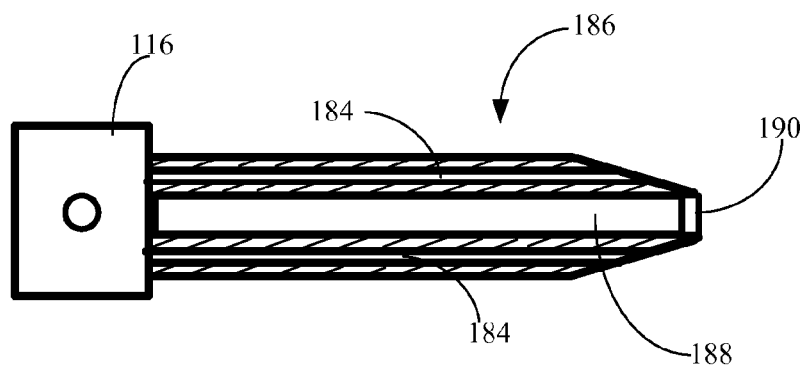
Figure 6C:
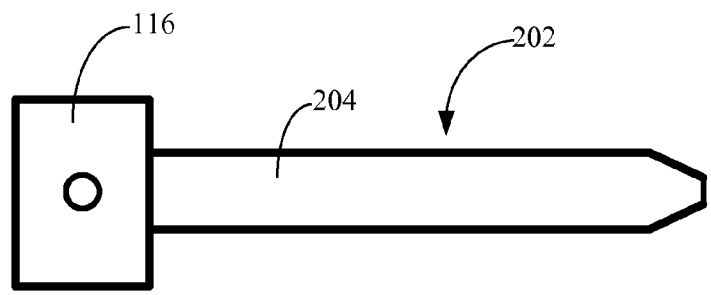

Controller 164 may further include a facility 168 for adipose tissue laser treatment products removal and a display 172, and/or a set of buttons providing a user interface and synchronizing operation of said source of laser radiation 160 with facility 168. Controller 164 further includes a temperature feedback loop 176 configured to receive temperature from a temperature sensor (see FIG. 8) and adapt laser power such as to provide safe tissue treatment. When laser radiation of proper power and wavelength is applied to adipose tissue, it liquefies the tissue and, in particular, the fat. The liquefied adipose tissue may be removed or may be left in the body, where it gradually dissipates through the body. FIGS. 6A-C, collectively referred to as FIG. 6 is a schematic illustration of the third exemplary embodiment of a disposable laser radiation conveying needle with liquefied fat removal channels. FIG. 6A is a cross section of a disposable needle 600. Needle 600 has a type of jacket 180 implemented as a structure containing a number of liquid conducting channels 184. Jacket 180 may be connected to facility 168, which may be a stand-alone facility or incorporated into controller 164 facility for liquefied fat and other adipose tissue laser treatment products removal. Needle 600 includes a solid light conducting core 620, a cladding 624 having a refractive index lower than core 620. A suction or vacuum provided by a pump (not shown) that is a part of facility 168 removes the liquefied tissue. Optical cable 156 (FIG. 5) may be implemented to have liquid conducting channels 184 in addition to optical fiber or a liquid collecting chamber communicating with a separate liquid conducting channel included in cable 156.

FIG. 6B illustrates a flexible or rigid needle 186 having a hollow light guide 188. The open end of guide 188, which is introduced into the adipose tissue, is terminated by a sapphire, diamond, or YAG window 190. Similar to needle 600 of FIG. 6A, needle 186 has channels 184 for liquefied fat and other adipose tissue laser treatment products removal.

FIG. 6C is an illustration of a needle 202 the body 204 of which is made of sapphire. Such needle is more resistant than plastic or glass needles to deposition on it of carbonized laser treatment products. Needle 202 may have a jacket (not shown) with liquid conducting channels. Alternatively, the jacket may be made of porous material with a suitable degree of porosity.

Figure 7:
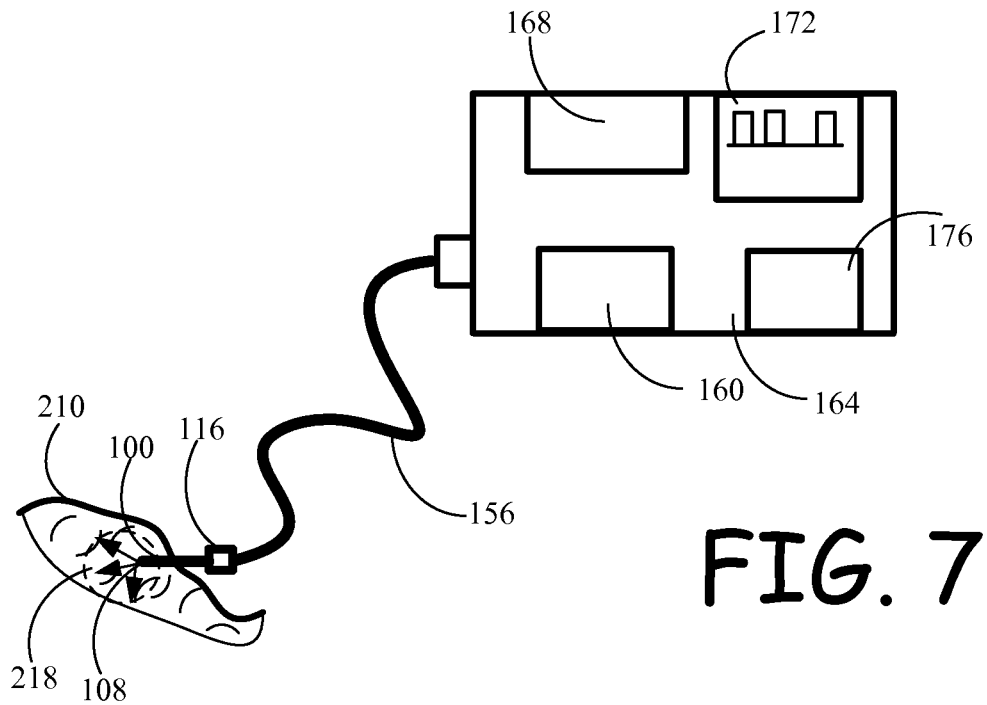
FIG. 7 is a schematic illustration of an apparatus and method of tissue treatment employing the present disposable laser radiation conveying needle.

FIG. 7 is a schematic illustration of the method of tissue treatment with the apparatus of various embodiments presented in the present disclosure, as well as embodiments not presented. For adipose tissue 210 treatment, needle 100, or any other needle described above or other needle embodiments incorporating one or more of the above-described elements, is connected by its second end 112 to a source of laser radiation 160 located in controller 164. First end 108 of needle 100 pierces the subject skin or tissue 210 and enables insertion of needle 100 into a target volume 218 of adipose tissue 210 to be treated. Controller 164 operates laser source 160 to irradiate target volume 218 of adipose tissue 210.

Radiation provided by one or more laser sources 160 liquefies at least a section of adipose tissue 210 adjacent to the first end 108 of needle 100. Controller 164 operates adipose tissue laser treatment products removal facility 168 that removes liquefied fat simultaneously with laser source 160.

In order to facilitate the process of tissue melting location observation an additional, second laser, visible through skin/tissue laser, such as a HeNe laser may be coupled to the needle or cable 156. This second laser, which is visible through skin, may assist the treatment provider in repositioning first end 108 of needle 100. In an alternative embodiment, a temperature sensitive cream, or a temperature sensitive liquid crystal paste, or a liquid crystal film may be spread on the tissue over the treated adipose tissue section. The paste/cream and the film may be such as Chromazone ink commercially available from Liquid Crystal Resources/Hallcrest, Inc. Glenview Ill. 60026 U.S.A. Needle 100 may be disposed of upon completion of treatment.

Figure 8:
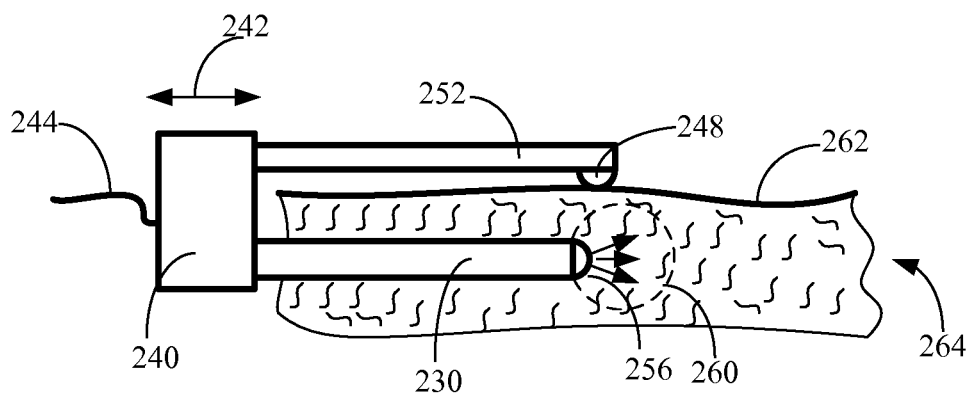
FIG. 8 is a schematic illustration of the forth exemplary embodiment of a disposable laser radiation conveying needle.

FIG. 8 is a schematic illustration of a forth exemplary embodiment of a disposable laser radiation conveying needle. Needle 230 is similar to any one of earlier described needles or may incorporate one or more of the afore-described aspects. It connects to a handle 240 which, with the help of optical cable 244, connects to controller 164. A temperature sensor 248 is mounted on a cantilever 252 configured to follow the first end 256 of needle 230 and measure the temperature of the tissue surface 262. Sensor 248 measures the temperature on the surface of the skin/tissue, and indicates or cuts-off the laser power when the treatment should be discontinued to avoid damage to the tissue surface 262. Temperature sensor 248 may be a contact sensor, being in contact with skin 262 or a non-contact sensor. During the treatment, the treatment provider moves handle 240 back and forth, as shown by arrow 242 within tissue 264. Temperature sensor 248 follows laser radiation emitting first end 256 of needle 230 and provides tissue/skin 262 temperature reading to controller 164 controlling the laser power coupled to the treated tissue volume 260. A feedback loop 176 of controller 164 is configured to read the temperature sensor and adapt laser power such as to provide safe tissue treatment. Cantilever 252 with temperature sensor 248 attached to it may be implemented as a part of handle 240 or as a removable and disposable or reusable part.

As disclosed above, source of laser radiation 160 may contain one or more laser sources operating at the same or different wavelengths. Accordingly, in an additional embodiment, laser beams from two laser sources with different wavelengths could be used to optimize simultaneous adipose tissue (or fat) destruction and blood hemostatis. The laser wavelengths may be, for example, 1,064 micrometer wavelength provided by a NdYAG laser and a 0.9 micrometer wavelength provided by a laser diode. Another suitable set of wavelengths is 1,064 micron and 0.532 micron. Such combination of laser wavelengths reduces bleeding, makes the fat removal procedure safer and shortens the patient recovery time.

In yet a further embodiment, two lasers guided through the same needle may operate each in different modes of operation. For example, a continuous wave (CW) laser with wavelength of 0.808 micron, 0.980 micron or about 1,500 micron may be delivered to target volume 218 (FIG. 7) of adipose tissue to preheat the volume to a desired temperature and liquefy the adipose tissue (fat).

Following this or almost simultaneously with a CW operating laser that heats-up the tissue, a pulsed IR laser, for example an Ho—(Holmium), Tm—(Thulium) or Er:Yag (Erbium Yttrium Aluminum Garnet) laser generating pulses in sub-millisecond or millisecond range may be applied to the same target tissue volume 218. During the course of the laser pulse, the target tissue (cells and intercellular fluid) near the end 108 of needle 100 changes to overheated (high-pressure) gas forming expanding micro bubbles collapsing at the end of the pulse. Mechanical stress developed by the pulsed laser action can increase the rate of membrane of adipose cells disruption and release of liquefied fat from the cell. This opto-mechanical action of laser radiation makes fat removal/suction more efficient.

FIG. 9 is a schematic illustration of an additional embodiment of an apparatus for laser assisted liposuction employing one of the afore-described needles or other needle embodiments including one or more of the afore-described aspects or elements. Fiber optics type connector 116 (FIGS. 1, 4, and 5) may be implemented as a T-type connector 236 where fluid/liquid conducting channels 184 (FIG. 6A) connect directly to laser treatment products removal facility 168 via a tube 274. This element simplifies cable 156 structure so that the cable 156 contains a light guide only.

The apparatus disclosed above may also be used for skin tightening. The needle is inserted subcutaneously into a treatment recipient so that the first end of the fiber is introduced within the tissue underlying the dermis. Laser source emits radiation of suitable power that is conveyed by the needle to the dermis, where the radiation causes collagen destruction and shrinkage within the treatment area.

Advantageously, the described embodiments of disposable needles enable continuous adipose tissue treatment process eliminates, or at least provides great attenuation in, the need for frequent needle removal, cleaning, and cleaving. Further, this advantageously significantly reduces the treatment time, makes the subject treatment more comfortable and simplifies the treatment process.

While the exemplary embodiments of the disposable needle and the method of using it have been illustrated and described, it will be appreciated that various changes can be made therein without affecting the spirit and scope of the needle and the method of using it. The scope of the needle and the method of using it, therefore, are defined by reference to the following claims presented herein.

What is claimed is:

1. A method for adipose tissue laser treatment, said method comprising:
   introducing into a target volume of adipose tissue a needle comprising a light conducting body having a first end being configured for introduction into adipose tissue and a second end, adapted to connect to a source of laser radiation including at least one laser operating in a continuous operation mode (CW) and at least one laser source operating in a pulse operation mode;
   causing the at least one laser in operating in continuous operation mode (CW) and the at least one laser source operating in a pulse operation mode to operate substantially simultaneously,
   wherein the laser operating in the continuous operation mode (CW) heats up the adipose tissue and the laser source operating in the pulse operation mode induces mechanical stress on the adipose tissue.

2. The method according to claim 1, wherein the laser operating in the continuous operation mode (CW) and the laser source operating in the pulse operation are at least one of a group of lasers consisting of a Ho—(Holmium) laser, Tm—(Thulium) laser or Er:Yag (Erbium Yttrium Aluminum Garnet) laser.

3. The method according to claim 1, wherein both laser sources affect the adipose tissue at the location being irradiated.

4. The method according to claim 1, further comprising monitoring the temperature of the target volume of the adipose tissue and adjusting the at least one laser source to avoid excessive damage to the target volume of adipose tissue; and
   wherein monitoring of temperature is performed by a temperature sensor mounted on a cantilever configured to follow the first end of the needle and measure the temperature of the tissue surface.

5. The method according to claim 1, further comprising operating simultaneously with one or more laser sources, a facility for adipose tissue laser removal.

6. The method according to claim 1, wherein at least two laser sources with different wavelengths are utilized to reduce bleeding.

7. The method according to claim 6, wherein the two lasers with different wavelengths are operating at a wavelength of 1,064 micrometers and a group of wavelengths consisting of a wavelength of 0.9 micrometers and a wavelength of 0.532 microns.

8. A disposable needle for introduction into and treatment of adipose tissue through the application of laser energy, the disposable needle comprising:
   a light conducting body having a receiving end configured to connect at least to a multiple-source of laser radiation; and
   the disposable needle being further configured to be removably coupled to two or more laser sources of the multiple-source of laser radiation, with at least one laser source operating in continuous (CW) operation mode and at least one laser source operating in pulse operation mode and the laser operating in continuous (CS) operation mode and the at least one laser source operating in pulse operation mode operating substantially simultaneously; and
   wherein the disposable needle is configured such that when introduced into an adipose tissue, the disposable needle delivers the laser operating in the continuous operation mode (CW) into the adipose tissue to cause the adipose tissue to be heated and the disposable needle delivers the laser source operating in the pulse operation mode such that mechanical stress is induced on the adipose tissue.

9. A method for using the needle of claim 8, said method comprising:
   connecting said needle to at least one source of laser radiation and operating the source of laser radiation;
   introducing the needle into a target volume of adipose tissue; and
   supplying laser radiation of sufficient power to convert at least a volume of the adipose tissue into a liquid.

10. The disposable needle according to claim 8, further comprising a temperature sensor located over the treated tissue volume and configured to follow the first end of the needle and measure the temperature of the surface of the tissue over the affected tissue volume.

11. The disposable needle according to claim 8, wherein the temperature sensor is one of a group of contact sensors or non-contact sensors.

12. The disposable needle according to claim 8, wherein the temperature sensor provides the temperature reading to a controller that controls laser power coupled to the treated skin volume.

13. The disposable needle according to claim 8, wherein:
   the laser that induces mechanical stress on the adipose tissue is at least one of a group of lasers consisting of a Ho—(Holmium) laser, Tm—(Thulium) laser or Er:Yag (Erbium Yttrium Aluminum Garnet); and
   the laser generates pulses in sub-millisecond or millisecond range.

14. The disposable needle according to claim 8, further comprising at least two lasers with one laser operating at a wavelength of 1,064 micrometer and a second laser operating at least at one of a group of wavelengths consisting of a wavelength of 0.9 micrometers and a wavelength of 0.532 microns.

* * * * *